(12) United States Patent
Luoma, II

(10) Patent No.: US 9,789,454 B2
(45) Date of Patent: *Oct. 17, 2017

(54) METHODS AND APPARATUS TO AGITATE A LIQUID

(71) Applicant: Abbott Laboratories, Abbott Park, IL (US)

(72) Inventor: Robert Paul Luoma, II, Colleyville, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/347,556

(22) Filed: Nov. 9, 2016

(65) Prior Publication Data

US 2017/0056848 A1    Mar. 2, 2017

Related U.S. Application Data

(63) Continuation of application No. 13/801,154, filed on Mar. 13, 2013, now Pat. No. 9,513,304.

(51) Int. Cl.
*B01F 9/00* (2006.01)
*B01L 9/06* (2006.01)
(Continued)

(52) U.S. Cl.
CPC .......... *B01F 9/0021* (2013.01); *B01F 9/0001* (2013.01); *B01F 9/004* (2013.01);
(Continued)

(58) Field of Classification Search
CPC .................................................... B01F 9/0018
(Continued)

(56) References Cited

U.S. PATENT DOCUMENTS 423,362 A * 3/1890 Wells .................... B01F 9/0021
366/214
3,994,594 A 11/1976 Sandrock et al.
(Continued)

FOREIGN PATENT DOCUMENTS

CA     2556772     9/2005
CN     1183057     5/1998
(Continued)

OTHER PUBLICATIONS

International Searching Authority, "Invitation to Pay Additional Fees," issued in connection with PCT Application No. PCT/US2013/078036, mailed Apr. 23, 2014, 7 pages.
(Continued)

*Primary Examiner* — David Sorkin
(74) *Attorney, Agent, or Firm* — Hanley, Flight & Zimmerman, LLC

(57) ABSTRACT

Method and apparatus to agitate a liquid are disclosed herein. An example apparatus includes a carrier having a base that includes a ridge extending from the base and a collar extending from the base. The example apparatus also includes a container supported on the base, the container movable between (A) a locked positon in which the ridge fixedly engages the container to non-rotatably couple the container to the base and (B) an unlocked position in which the container is disengaged from the ridge and the container is rotatable about the collar.

18 Claims, 12 Drawing Sheets

(51) Int. Cl.
  *B01F 11/00* (2006.01)
  *B01L 3/00* (2006.01)
  *G01N 35/02* (2006.01)
  *G01N 35/10* (2006.01)
  *G01N 35/04* (2006.01)
  *G01N 35/00* (2006.01)

(52) U.S. Cl.
  CPC ...... *B01F 11/0002* (2013.01); *B01F 11/0008* (2013.01); *B01L 3/527* (2013.01); *B01L 9/06* (2013.01); *G01N 35/025* (2013.01); *G01N 35/04* (2013.01); *G01N 35/1002* (2013.01); *B01F 2009/0092* (2013.01); *B01F 2215/0037* (2013.01); *B01L 2200/025* (2013.01); *B01L 2300/0861* (2013.01); *G01N 2035/00465* (2013.01); *G01N 2035/0443* (2013.01); *G01N 2035/0451* (2013.01)

(58) Field of Classification Search
  USPC ......... 220/629; 366/225, 228, 229; 422/554, 422/562
  See application file for complete search history.

(56) References Cited

U.S. PATENT DOCUMENTS

| | | | |
|---|---|---|---|
| D273,987 S | 5/1984 | Holen et al. | |
| 4,515,753 A | 5/1985 | Smith et al. | |
| 4,557,600 A | 12/1985 | Klose et al. | |
| 4,684,614 A | 8/1987 | Krovak et al. | |
| 4,705,668 A | 11/1987 | Kaltenbach et al. | |
| D297,166 S | 8/1988 | Hollar et al. | |
| 4,849,177 A | 7/1989 | Jordan | |
| 4,883,763 A | 11/1989 | Holen et al. | |
| 5,005,721 A | 4/1991 | Jordan | |
| 5,128,104 A | 7/1992 | Murphy et al. | |
| 5,324,481 A | 6/1994 | Dunn et al. | |
| D355,260 S | 2/1995 | Tomasso | |
| 5,417,922 A | 5/1995 | Markin et al. | |
| D365,153 S | 12/1995 | Robertson, Jr. | |
| 5,578,272 A | 11/1996 | Koch et al. | |
| 5,632,399 A | 5/1997 | Palmieri et al. | |
| 5,758,786 A * | 6/1998 | John .................. A61J 11/045 215/11.1 | |
| 5,788,928 A | 8/1998 | Carey et al. | |
| 5,811,296 A | 9/1998 | Chemelli et al. | |
| 5,830,411 A | 11/1998 | Martinell Gisper-Sauch | |
| D404,831 S | 1/1999 | Yamazaki et al. | |
| D411,014 S | 6/1999 | Berger et al. | |
| 5,968,453 A | 10/1999 | Shugart | |
| 6,066,300 A | 5/2000 | Carey et al. | |
| D433,149 S | 10/2000 | Fassbind et al. | |
| 6,149,872 A | 11/2000 | Mack et al. | |
| 6,190,617 B1 | 2/2001 | Clark et al. | |
| 6,190,619 B1 | 2/2001 | Kilcoin et al. | |
| 6,299,567 B1 | 10/2001 | Forrest et al. | |
| 6,319,719 B1 | 11/2001 | Bhullar et al. | |
| 6,375,030 B1 | 4/2002 | Spickelmire | |
| 6,386,749 B1 | 5/2002 | Watts et al. | |
| 6,431,388 B1 | 8/2002 | Spickelmire et al. | |
| 6,432,359 B1 | 8/2002 | Carey et al. | |
| 6,458,526 B1 | 10/2002 | Schembri et al. | |
| 6,509,193 B1 | 1/2003 | Tajima | |
| 6,511,634 B1 | 1/2003 | Bradshaw et al. | |
| 6,517,783 B2 | 2/2003 | Horner et al. | |
| 6,537,505 B1 | 3/2003 | LaBudde et al. | |
| D482,454 S | 11/2003 | Gebrian | |
| 6,866,820 B1 | 3/2005 | Otto et al. | |
| D531,736 S | 11/2006 | Gomm et al. | |
| D532,524 S | 11/2006 | Gomm et al. | |
| D533,947 S | 12/2006 | Gomm et al. | |
| D534,280 S | 12/2006 | Gomm et al. | |
| 7,182,912 B2 | 2/2007 | Carey et al. | |
| 7,238,521 B2 | 7/2007 | Hahn et al. | |
| 7,458,483 B2 | 12/2008 | Luoma, II | |
| 7,485,118 B2 | 2/2009 | Blankenstein et al. | |
| 7,615,370 B2 | 11/2009 | Streit et al. | |
| 7,628,954 B2 | 12/2009 | Gomm et al. | |
| 7,731,414 B2 | 6/2010 | Vincent et al. | |
| 7,736,907 B2 | 6/2010 | Blankenstein et al. | |
| D620,603 S | 7/2010 | Talmer et al. | |
| 7,794,656 B2 | 9/2010 | Liang et al. | |
| D630,765 S | 1/2011 | Winkenbach et al. | |
| D632,402 S | 2/2011 | Sattler et al. | |
| 7,897,379 B2 | 3/2011 | Kenney et al. | |
| D637,731 S | 5/2011 | Sattler et al. | |
| 7,951,344 B2 | 5/2011 | Kikuchi et al. | |
| 7,964,140 B2 | 6/2011 | Watari | |
| D645,973 S | 9/2011 | Hoenes | |
| 8,017,094 B2 * | 9/2011 | Meyer ................ B01F 11/0008 366/110 |
| 8,133,721 B2 | 3/2012 | Yang et al. | |
| 8,187,558 B2 | 5/2012 | Jacobs et al. | |
| D665,095 S | 8/2012 | Wilson et al. | |
| D666,736 S | 9/2012 | Kobayashi | |
| D672,881 S | 12/2012 | Kraihanzel | |
| 8,535,624 B2 | 9/2013 | Luoma, II | |
| D696,419 S | 12/2013 | Fusellier et al. | |
| 9,149,979 B2 | 10/2015 | Sattler et al. | |
| 9,304,140 B2 | 4/2016 | Wakamiya | |
| 9,535,082 B2 * | 1/2017 | Luoma, II ............... G01N 35/04 |
| 2002/0169518 A1 | 11/2002 | Luoma, II | |
| 2003/0044323 A1 | 3/2003 | Diamond et al. | |
| 2003/0129766 A1 | 7/2003 | Kawamura et al. | |
| 2004/0005714 A1 | 1/2004 | Safar et al. | |
| 2004/0134750 A1 | 7/2004 | Luoma, II | |
| 2005/0106756 A1 | 5/2005 | Blankenstein et al. | |
| 2006/0087911 A1 | 4/2006 | Herz et al. | |
| 2006/0263248 A1 | 11/2006 | Gomm et al. | |
| 2006/0286004 A1 | 12/2006 | Jacobs et al. | |
| 2007/0010019 A1 | 1/2007 | Luoma, II | |
| 2007/0166193 A1 | 7/2007 | Veen et al. | |
| 2008/0056948 A1 | 3/2008 | Dale et al. | |
| 2008/0064090 A1 | 3/2008 | Whittlinger | |
| 2008/0226513 A1 | 9/2008 | Morbidelli et al. | |
| 2008/0317632 A1 | 12/2008 | Shimasaki et al. | |
| 2009/0004058 A1 | 1/2009 | Liang et al. | |
| 2009/0215159 A1 | 8/2009 | Kirby | |
| 2009/0325309 A1 | 12/2009 | Favuzzi et al. | |
| 2010/0092343 A1 | 4/2010 | Nemeth | |
| 2010/0111765 A1 | 5/2010 | Gomm et al. | |
| 2010/0190265 A1 | 7/2010 | Dufva et al. | |
| 2010/0276445 A1 | 11/2010 | Jacobs et al. | |
| 2012/0087830 A1 | 4/2012 | Wakamiya | |
| 2012/0141339 A1 | 6/2012 | Sattler et al. | |
| 2012/0195808 A1 | 8/2012 | Arras et al. | |
| 2012/0218854 A1 | 8/2012 | Behringer et al. | |
| 2013/0059376 A1 | 3/2013 | Justice et al. | |
| 2015/0010443 A1 | 1/2015 | Hasegawa | |
| 2015/0224500 A1 | 8/2015 | Brueckner et al. | |

FOREIGN PATENT DOCUMENTS

| | | |
|---|---|---|
| CN | 1726288 | 1/2006 |
| CN | 101439274 | 5/2009 |
| EP | 435481 | 7/1991 |
| EP | 1687080 | 11/2003 |
| EP | 1855114 | 11/2007 |
| EP | 1733794 | 9/2010 |
| EP | 2255880 | 12/2010 |
| GB | 1307086 | 2/1973 |
| JP | S27758 | 3/1977 |
| JP | S58134773 | 9/1983 |
| JP | H10228689 | 8/1998 |
| JP | 2000009726 | 1/2000 |
| JP | 2003194828 | 7/2003 |
| JP | 2004061160 | 2/2004 |
| JP | 2005017176 | 1/2005 |
| JP | 2005181338 | 7/2005 |
| JP | 2006125897 | 5/2006 |
| JP | 2007309740 | 11/2007 |
| JP | 2008026221 | 2/2008 |
| JP | 4268212 | 5/2009 |

(56) References Cited

FOREIGN PATENT DOCUMENTS

| JP | 2009276252 | 11/2009 |
|---|---|---|
| JP | 2009544959 | 12/2009 |
| WO | 9634681 | 11/1996 |
| WO | 03020427 | 3/2003 |
| WO | 2006119361 | 11/2006 |
| WO | 2007125642 | 11/2007 |
| WO | 2009131705 | 10/2009 |

OTHER PUBLICATIONS

International Searching Authority, "International Search Report and Written Opinion," issued in connection with PCT Application No. PCT/US2013/078036, mailed Jun. 25, 2014, 17 pages.

International Searching Authority, "International Preliminary Report on Patentability," issued in connection with PCT Application No. PCT/US2013/078036, mailed Sep. 24, 2015, 12 pages.

European Patent Office, "Communication pursuant to Rules 161(1) and 162 EPC," issued in connection with European Patent Application No. 13821412.7, dated Oct. 28, 2015, 2 pages.

United States Patent and Trademark Office, "Advisory Action," issued in connection with U.S. Appl. No. 13/801,451, mailed Dec. 7, 2015, 11 pages.

United States Patent and Trademark Office, "Restriction and/or Election Requirement," issued in connection with U.S. Appl. No. 29/531,426, mailed Aug. 18, 2016, 9 pages.

United States Patent and Trademark Office, "Restriction and/or Election Requirement," issued in connection with U.S. Appl. No. 29/531,434, mailed Sep. 6, 2016, 9 pages.

State Intellectual Property Office of China, "First Office Action," issued in connection with Chinese Patent Application No. 201380076523.8, dated Oct. 18, 2016, 8 pages.

Japanese Patent Office, "Notice of Rejection," issued in connection with Japanese Patent Application No. 2016-500148, mailed Sep. 6, 2016, 11 pages.

State Intellectual Property Office of China, "Notice of Grant of Patent Right for a Design," issued in connection with Chinese Patent Application No. 201630099345.7, dated May 19, 2016, 5 pages.

State Intellectual Property Office of China, "Notice of Grant of Patent Right for a Design," issued in connection with Chinese Patent Application No. 201630099342.3, dated May 19, 2016, 5 pages.

United States Patent and Trademark Office, "Ex parte Quayle Action," issued in connection with U.S. Appl. No. 29/431,426, mailed Dec. 30, 2016, 11 pages.

United States Patent and Trademark Office, "Non-Final Office Action," issued in connection with U.S. Appl. No. 13/801,451, mailed Aug. 12, 2016, 20 pages.

State Intellectual Property Office of China, "First Office Action," issued in connection with Chinese Patent Application No. 201380076521.9, dated Jul. 13, 2016, 22 pages.

Japanese Patent Office, "Notice of Rejection," issued in connection with Japanese Patent Application No. 2016-500147, mailed Oct. 4, 2016, 13 pages.

United States Patent and Trademark Office, "Notice of Allowance," issued in connection with U.S. Appl. No. 13/801,154, mailed Apr. 5, 2016, 17 pages.

United States Patent and Trademark Office, "Non-Final Office Action," issued in connection with U.S. Appl. No. 13/801,154, mailed Oct. 5, 2015, 25 pages.

United States Patent and Trademark Office, "Election and/or Restriction Requirement," issued in connection with U.S. Appl. No. 13/801,154, mailed Jul. 14, 2015, 7 pages.

United States Patent and Trademark Office, "Ex parte Quayle Action," issued in connection with U.S. Appl. No. 29/531,434, mailed Jan. 26, 2017, 15 pages.

State Intellectual Property Office of China, "Second Office Action," issued in connection with Chinese Patent Application No. 201380076521.9, dated Feb. 3, 2017, 23 pages.

United States Patent and Trademark Office, "Final Office Action," issued in connection with U.S. Appl. No. 13/801,451, mailed Feb. 24, 2017, 44 pages.

United States Patent and Trademark Office, "Restriction and/or Election Requirement," issued in connection with U.S. Appl. No. 29/531,426, mailed May 16, 2016, 9 pages.

United States Patent and Trademark Office, "Restriction and/or Election Requirement," issued in connection with U.S. Appl. No. 29/531,434, mailed May 10, 2016, 9 pages.

European Patent Office, "Communication pursuant to Article 94(3) EPC," issued in connection with European Patent No. 13 821 411.9, dated Jun. 7, 2017, 8 pages.

United States Patent and Trademark Office, "Non-Final Office Action," issued in connection with U.S. Appl. No. 13/801,451, dated Jun. 15, 2017, 27 pages.

State Intellectual Property Office of China, "Second Office Action," issued in connection with Chinese Patent Application No. 201380076523.8, dated Jun. 12, 2017, 14 pages.

United States Patent and Trademark Office, "Notice of Non-Compliant Amendment," issued in connection with U.S. Appl. No. 29/531,426, dated Jun. 29, 2017, 15 pages.

United States Patent and Trademark Office, "Notice of Non-Compliant Amendment," issued in connection with U.S. Appl. No. 29/531,434, dated Jun. 29, 2017, 15 pages.

* cited by examiner

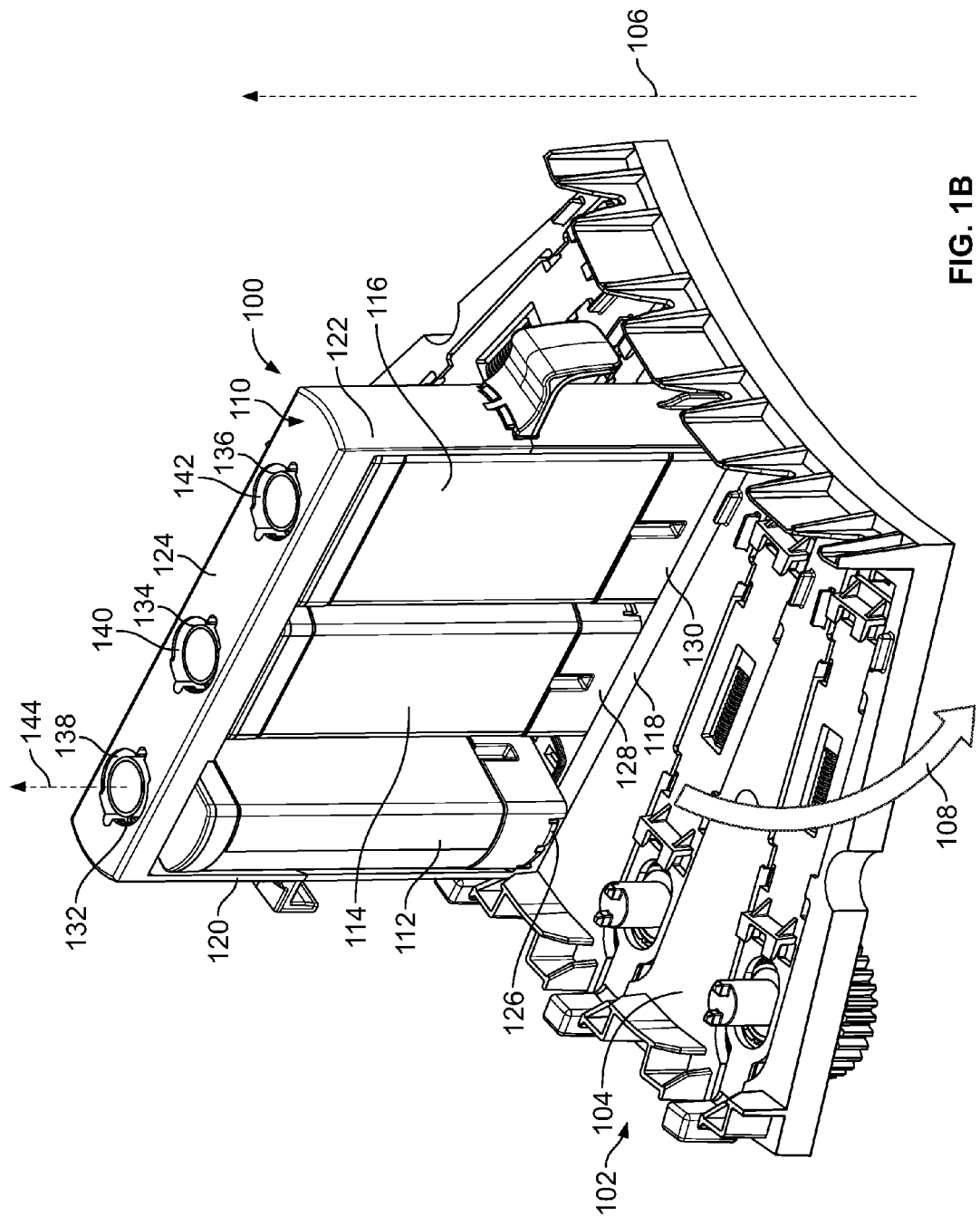

METHODS AND APPARATUS TO AGITATE A LIQUID

RELATED APPLICATION

This patent arises from a continuation of U.S. application Ser. No. 13/801,154, titled "METHODS AND APPARATUS TO AGITATE A LIQUID," and filed Mar. 13, 2013. U.S. application Ser. No. 13/801,154 is incorporated herein by this reference in its entirety.

FIELD OF THE DISCLOSURE

This disclosure relates generally to fluid analyzers and, more particularly, to methods and apparatus to agitate a liquid.

BACKGROUND

Automated analyzers are used to analyze samples including biological material gathered from patients for diagnostic purposes. Generally, analysis of a sample involves reacting the sample with one or more reagents in a liquid container. Some automated analyzers store reagents in containers on a carousel. When a particular reagent is needed, the carousel is rotated to move the container holding the reagent to be adjacent an aspirating/dispensing device. The carousel moves by accelerating and decelerating, which subjects the reagents to rotational forces that could cause microparticles to be suspended in the reagents. However, some of the microparticles in the container may accumulate at the bottom of the container.

BRIEF DESCRIPTION OF THE DRAWINGS

FIG. 1B illustrates the example cartridge of FIG. 1A with the first container in a second position.

Figure 1A:
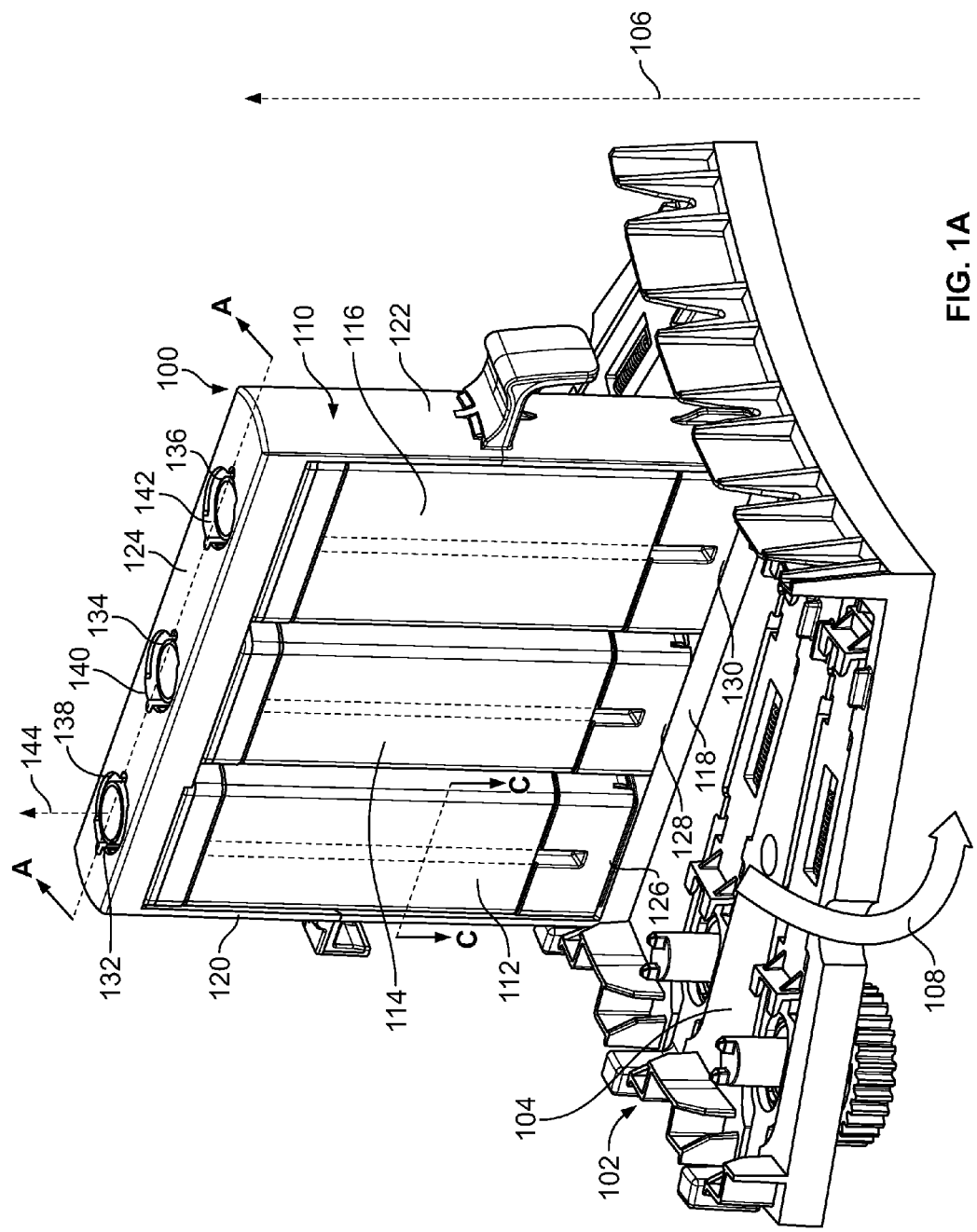
FIG. 1A illustrates an example cartridge that is holding a plurality of example containers and which is coupled to a portion of an example carousel with a first container in a first position.

Some of the figures or some of the portions of the figures may not be to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part (e.g., a layer, film, area, or plate) is in any way positioned on (e.g., positioned on, located on, disposed on, or formed on, etc.) another part, means that the referenced part is either in contact with the other part, or that the referenced part is above the other part with one or more intermediate part(s) located therebetween. Stating that any part is in contact with another part means that there is no intermediate part between the two parts.

DETAILED DESCRIPTION

Disclosed herein are methods and apparatus to agitate a liquid such as, for example, a liquid reagent in a container of an automatic diagnostic analyzer, which may be, for example, a clinical chemistry analyzer, an immunoassay analyzer, and/or a hematology analyzer. Some reagents used in automatic diagnostic analyzers include a liquid and microparticles, where the microparticles are to be mixed and, in some examples, substantially uniformly dispersed in the liquid. Automatic diagnostic analyzers typically rotate reagent containers or bottles about an axis and the rotation imparts forces on the contents of the containers to mix the contents. Traditional reagent bottles are cylindrical and include internal fins that are used to mix and disperse particles in the liquid of the reagent.

The examples disclosed herein use rectangular, rounded rectangular or substantially rectangularly-shaped reagent containers. The examples disclosed herein achieve uniform mixing and dispersion of reagents such as, for example, reagents including microparticles. These disclosed examples provide greater space utilization in diagnostic systems than many known configurations. As a result, using examples described herein, analyzers can have an increased load capacity and/or smaller size, compared to many known systems. In some examples, one of the containers or bottles is about 20 millimeters (mm) deep, about 36 mm wide and about 92 mm high. Other examples may have other dimensions. Another advantage of the disclosed examples is that the example bottles can be created with fabrication techniques such as, for example, blow molding, that reduce cost compared to the fabrication techniques of many known configurations.

In the examples disclosed herein, flat opposing sides of the example bottles create a mixing action in a liquid in the bottle in response to acceleration and deceleration of the bottles. An example bottle disclosed herein is rotated about its central longitudinal axis in an oscillating manner. In addition, the bottle is coupled to a cartridge that is rotated about a rotational axis of a carousel. The bottle and a cap include features, as disclosed herein, that provide bearing surfaces for rotation of the bottle. The bottle may be composed of a material or materials to enable one or more surfaces of the bottle to function as a disposable bearing. In some examples, the bottle may be composed of a high density polyethlyene that has excellent wear characteristics and which can withstand, for example, a 30-day on-board use period (e.g., continuous use on a diagnostic analyzer)

with negligible wear. The acceleration and deceleration and the rectangular walls impart forces on the liquid in the bottle to promote mixing of the contents of the bottle. A rounded or curved bottom of the interior of the bottle also aids in mixing by creating upward motion on particles that may accumulate at the bottom of the bottle as a result of settling that occurs when the bottle is stationary. More specifically, centrifugal force created by the rotation of the bottle moves such settled particles out from the center of the bottom of the bottle and lifts the particles as the particles follow the contour of the bottle bottom. In some examples, visible confirmation of a uniform mixing is achieved in about one minute of oscillating motion. Other mixing periods and oscillation rates may be used depending on the reagent(s) used, the microparticle(s) used, the diagnostic test(s) to be conducted and/or other factors.

Disclosed herein is an example apparatus that includes a base, a first end wall and a second end wall. The example apparatus also includes a first container and a second container having a rounded rectangular cross-sectional shape and forming a rounded rectangular block i.e., a bar-shaped object having rounded edges (collectively referred to as a rounded rectangular shape). In addition, the example apparatus includes a first container support to retain the first container The example first container support includes first posts to engage a first rim of the first container to non-rotatably couple the first container to the base. Also, the example apparatus includes a second container support to retain the second container. The example second container support includes a collar to engage a groove of the second container and a ridge to engage a second rim of the second container. The example second container is selectively rotatable relative to the base.

In some examples, the example apparatus also includes a third container support to retain a third container. The example third container support includes second posts to engage a third rim of the third container to non-rotatably couple the third container to the base.

In some examples, the apparatus is to rotate about a first axis of rotation, and the second container is to rotate relative to the base about a second axis of rotation.

In some examples, the second container is movable between a locked position in which the second rim of the second container is engaged with the ridge to non-rotatably couple the second container to the base and an unlocked position in which the second container is raised so that the second rim is disengaged from the ridge and the groove is rotatable about the collar.

In some examples, the apparatus includes a cover having a first aperture to access the first container and a second aperture to access the second container.

Also disclosed herein is an example apparatus that includes a first sidewall and a second sidewall substantially parallel to the first sidewall. The example apparatus also includes a top wall coupled to the first sidewall and the second sidewall. The example apparatus further includes a bottom wall opposite the top wall and coupled to the first sidewall and the second sidewall. The bottom wall has a first side to define a cavity to hold a liquid. The example apparatus also includes a protrusion extending from the first side of the bottom wall toward the top wall.

In some examples, the protrusion is disposed on a center of the bottom wall. Also, in some examples, the protrusion is disposed on an axis of rotation of the bottom wall. In addition, in some examples, the protrusion has an apex disposed along an axis of rotation of the bottom wall.

In some examples, the example apparatus includes a third sidewall and a fourth sidewall opposite the third sidewall. In this example, the third sidewall and the fourth sidewall are curved.

In some examples, the bottom wall has a first radius of curvature, and the protrusion has a second radius of curvature different than the first radius of curvature. In some examples, the first radius of curvature is oriented in a first direction and the second radius of curvature is oriented in a second direction different than the first direction.

In some examples, the first sidewall includes a rib extending toward the second sidewall. Also, in some examples, the apparatus includes a post depending from a first side of the bottom wall. In such examples, the protrusion extends from a second side of the bottom wall. In some examples, the post defines a plurality of notches. Also, in some examples, the notches are engageable with a rotation mechanism to rotate the apparatus about an axis of rotation aligned with the concave portion, i.e., coaxial with a central axis of the concave portion.

In some examples, the first sidewall includes a first planar portion and the second sidewall includes a second planar portion. In addition, in some examples, the example apparatus includes a third sidewall and a fourth sidewall opposite the third sidewall. In such examples, at least two of the first sidewall, second sidewall, third sidewall or fourth sidewall include a rim to engage a ridge on a carrier to hold the container in a non-rotatable position.

Also disclosed herein is an example method that includes lifting a first container from a first position in which a rim of the first container is engaged with a ridge of a carrier and a groove of the first container is engaged with a collar of the carrier to a second position in which the rim is disengaged from the ridge and the groove is engaged with the collar. The example method also includes rotating the first container about an axis of rotation and mixing contents of the first container. In such examples, the contents are mixed by a first substantially flat sidewall of the first and a bottom protrusion of the first container.

In some examples, the example method includes non-rotatably supporting a second container on the carrier while rotating the first container. In addition, in some examples, the example method includes lowering the first container to the first position to non-rotatably couple the first container to the carrier.

Turning now to the figures, FIG. 1A is a perspective view of an example cartridge 100 coupled to a carousel 102 of a diagnostic analyzer. In the illustrated example, the carousel 102 includes a platform 104 on which the cartridge 100 is supported. The cartridge 100 may be transported to and/or placed on the platform 104 manually, by a robotic device, via a conveyer, and/or via any other device and/or technique. During operation of the example carousel 102, the platform 104 and, thus, the cartridge 100 rotates about a first axis of rotation 106 along a substantially circular path 108 defined by the carousel 102. In some examples, multiple cartridges are coupled to the platform 104.

In some examples, the platform 104 moves periodically or aperiodically in one direction, e.g., in the direction of path 108. In other examples, the platform 104 moves in a back-and-forth (e.g., oscillating) motion. For example, the platform 104 may repeatedly move a first distance in a first direction (e.g., clockwise) and then a second distance in a second direction (e.g., counterclockwise) opposite the first direction. In some examples, the first direction is greater than the second direction such that the cartridge 100 on the platform 104 revolves about the first axis of rotation 106 via the back-and-forth motion. In some examples, after the platform 104 moves in the first direction, the platform 104 is substantially stationary for a given amount of time before moving in the second direction.

In the illustrated example, the cartridge 100 includes a base or carrier 110, a first container 112, a second container 114 and a third container 116. In some examples, there may be other numbers of containers, including, for example, one, two, four, five, six, etc. Also, in some examples, one or more containers may be divided into a multiple compartments to increase the number of compartments on a carrier. Thus, a carrier could include three containers, and one container could have three compartments so that there are a total of five compartments on a carrier. Other combinations are possible. In the illustrated example, the carrier 110 is coupled to the platform 104 to rotate with the platform 104. The example carrier 110 includes a seat 118, a first end wall 120, a second end wall 122 and a cover 124. In the illustrated example, first ends 126, 128, 130 of the first container 112, the second container 114 and the third container 116, respectively, are coupled to the seat 118, and second ends 132, 134, 136 of the first container 112, the second container 114 and the third container 116, respectively, are coupled to the cover 124.

In the illustrated example, the first container 112, the second container 114 and the third container 116 are arranged in the carrier 110 radially relative to the circular path 108 defined by carousel 102. In the illustrated example, the first container 112 is disposed adjacent the first end wall 120, the third container 116 is disposed adjacent the second end wall 122, and the second container 114 is disposed between the first container 112 and the second container 114. The example containers 112, 114, 116 have rounded-rectangular shapes. In other examples, the containers 112, 114, 116 have other shapes (e.g., rectangular, square, cylindrical, triangular shapes or other suitable shapes). Each of the containers 112, 114, 116 is to hold a liquid. In some examples, the liquid includes a sample to be analyzed, one or more reagents and/or solid particles (e.g., latex coated paramagnetic particles and/or other microparticles). The example cover 124 includes three apertures 138, 140, 142 to provide access to the containers 112, 114, 116. For example, the liquid may be deposited into and/or removed from the first container 112, the second container 114 and the third container 116 via the respective apertures 138, 140, 142. In some examples, the first container 112, the second container 114 and/or the third container 116 have about the same liquid volume capacity. In other examples, the first container 112, the second container 114 and/or the third container 116 have different liquid volume capacities. The first container 112, the second container 114 and/or the third container 116 may be filled with the same amount or different amounts of liquid.

FIG. 1B is a perspective view of the example cartridge 100 as the first container 112 is rotated relative to the carrier 110 about a second axis of rotation 144. In the illustrated example, the first container 112 is coupled to the carrier 110 to enable the first container 112 to rotate with the carrier 110 about the first axis of rotation 106 and relative to the carrier 110 about a second axis of rotation 144. In some examples, the rotation of the first container 112 relative to the carrier 110 corresponds to the movement of the platform 104. In the illustrated example, as the cartridge 100 moves in the first direction with the platform 104, the first container 112 is rotated two revolutions relative to the carrier 110 in the first direction. As the cartridge 100 moves in the second direction with the platform 104, the first container 112 moves one revolution relative to the carrier 110 in the second direction. In this manner, the first container 112 moves in a back-and-forth and/or oscillating motion relative to the carrier 110. The above-noted numbers of revolutions of the first container 112 relative to the carrier 110 in the first direction and the second direction and the manner (e.g., the back-and-forth movement) in which the container moves relative to the carrier 110 are merely examples. In other examples, the first container 112 rotates relative to the carrier 110 in other manners, numbers of revolutions, directions, etc. In some examples, the first container 112 rotates fully about the second axis of rotation 144, and in some examples, the first container 112 oscillates back and forth about the second axis of rotation 144. Also, in some examples, the first container 112 moves about the second axis of rotation 144 while the carousel 102 is stationary relative to the first axis of rotation 106.

Figure 2:
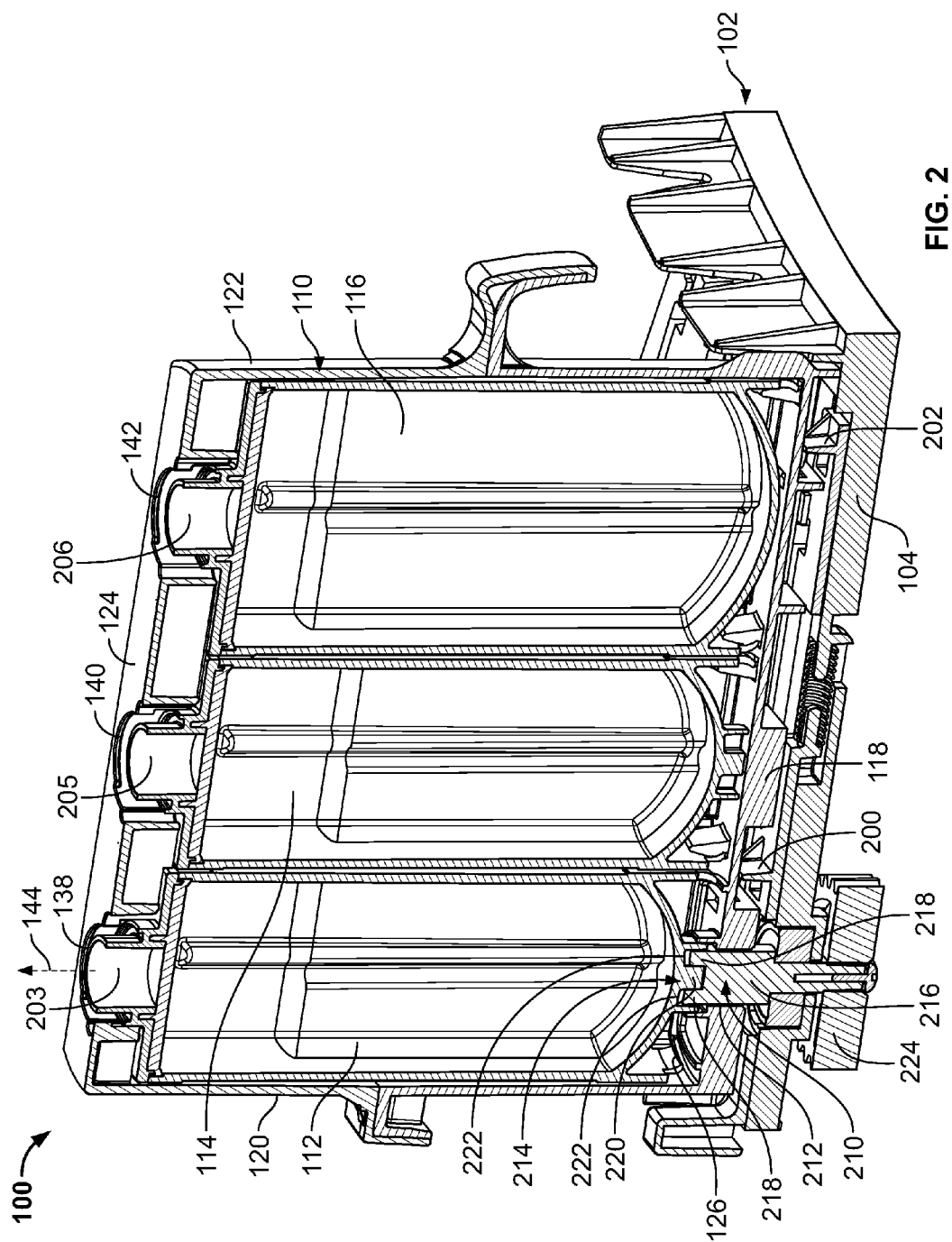
FIG. 2 is a cross-sectional view taken along the A-A line of FIG. 1A.

FIG. 2 is a cross-sectional view of the example cartridge 100 coupled to the carousel 102 taken along the A-A line of FIG. 1A. The example cartridge 100 is removably coupled to the carousel 102 via the carrier 110. In the illustrated example, the platform 104 includes a first prong 200 and a second prong 202 to engage corresponding structures (e.g., apertures, female connectors, etc.) on the carrier 110 and hold the carrier 110 in place relative to the platform 104. In other examples, the cartridge 100 is removably coupled to the carousel 102 in other manners (e.g., via one or more clamps, clips, bolts, snaps, spring-loaded pins, and/or other mechanical fasteners).

In the illustrated example, the first container 112, the second container 114 and the third container 116 each includes a throat 203, 205, 206 (e.g., a tube or pipe in fluid communication with one of the containers 112, 114, 116) in communication with (e.g., extending into) one of the apertures 138, 140, 142 of the cover 124. During operation of the example carousel 102, liquid may be dispensed (e.g., deposited) and/or aspirated (e.g., removed) from the containers 112, 114, 116 via the throats 203, 205, 206 (e.g., via a pipette).

In the illustrated example, the second container 114 and the third container 116 are coupled to the carrier 110 such that the second container 114 and the third container 116 are substantially stationary relative to the carrier 110 during operation of the carousel 102 (e.g., as the platform 104 moves the cartridge 100 along the circular path 108).

In the illustrated example, the carousel 102 includes a coupling 210 to rotate the first container 112 relative to the carrier 110 about the second axis of rotation 144. In the illustrated example, the seat 118 of the carrier 110 defines a fourth aperture 212 adjacent the first end 126 of the first container 112. In the illustrated example, the coupling 210 extends from beneath the platform 104 in the orientation of FIG. 2 through the fourth aperture 212 to engage the first container 112. As described in greater detail below in conjunction with FIG. 8, the coupling 210 lifts the first container 112 from the seat 118 to enable the first container 112 to rotate relative to the carrier 110 about the second axis of rotation 144.

The example coupling 210 of FIG. 2 is a male connector to engage a female connector 214 disposed on the first end 126 of the example first container 112. In other examples, the male connector 210 and the female connector 214 may be reversed. In the illustrated example, the male coupling 210 includes a shaft 216 having protrusions 218, and the example female connector 214 includes a post 220 having notches 222 to receive the protrusions 218 of the shaft 216. In the illustrated example, the coupling 210 is operatively coupled to a rotation mechanism 224 (e.g., a gear). The rotation mechanism 224 is operatively coupled to a drive mechanism (e.g., a motor) (not shown) of the carousel 102.

In some examples, as the carousel 102 rotates the platform 104 about the first axis of rotation 106, the rotation mechanism 224 and the coupling 210 are rotated about the second axis of rotation 144 to rotate the first container 112 about the second axis of rotation 144 relative to the carrier 110. Thus, in the illustrated example, the coupling 210 defines the second axis of rotation 144. In the illustrated example, the second axis of rotation 144 is substantially parallel to a longitudinal axis of the first container 112.

Figure 3:
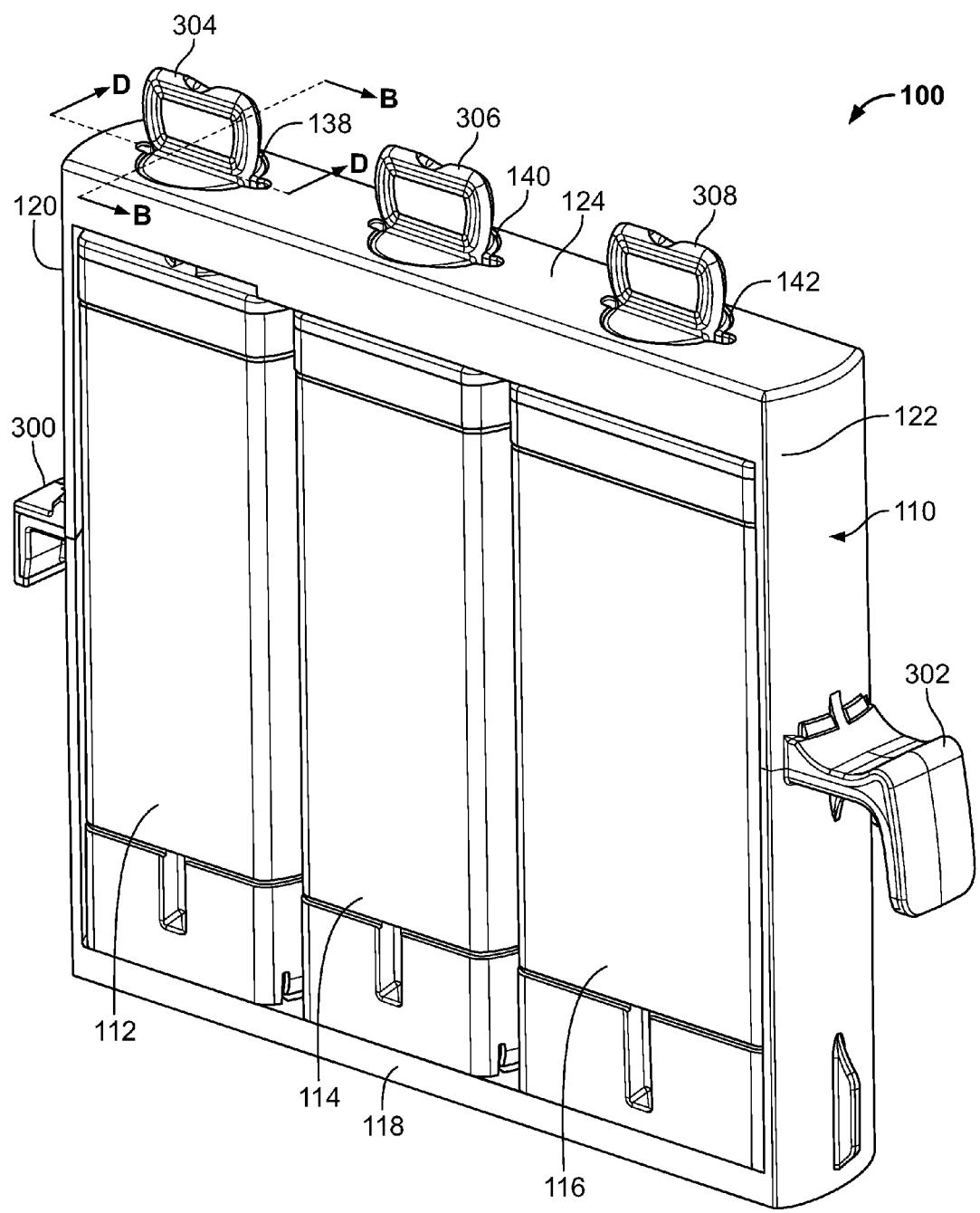
FIG. 3 is a perspective view of the example cartridge and containers of FIGS. 1A and 2 decoupled from the carousel and sealed.

FIG. 3 is a perspective view of the example cartridge 100 decoupled from the carousel 102 of FIGS. 1A-2. In the illustrated example, the carrier 110 includes a first handle 300 and a second handle 302 to facilitate grasping, holding, lifting, maneuvering and/or transporting of the cartridge 100 by a human (e.g., manually) and/or a robot. In the illustrated example, a first cap 304 is coupled to the first container 112, a second cap 306 is coupled to the second container 114 and a third cap 308 is coupled to the third container 116. The caps 304, 306, 308 substantially cover and/or seal the throats 203, 205, 206 of the containers 112, 114, 116. In some examples, the first container 112, the second container 114 and/or the third container 116 are at least partially filled with liquid before the cartridge 100 is coupled to the carousel 102. Thus, the example caps 304, 306, 308 prevent liquid from flowing out of the containers 112, 114, 116 while the cartridge 100 is being lifted, handled, maneuvered, transported, etc. As described in greater detail below, the example first cap 304 may hold the first container 112 in a locked position.

Figure 4:
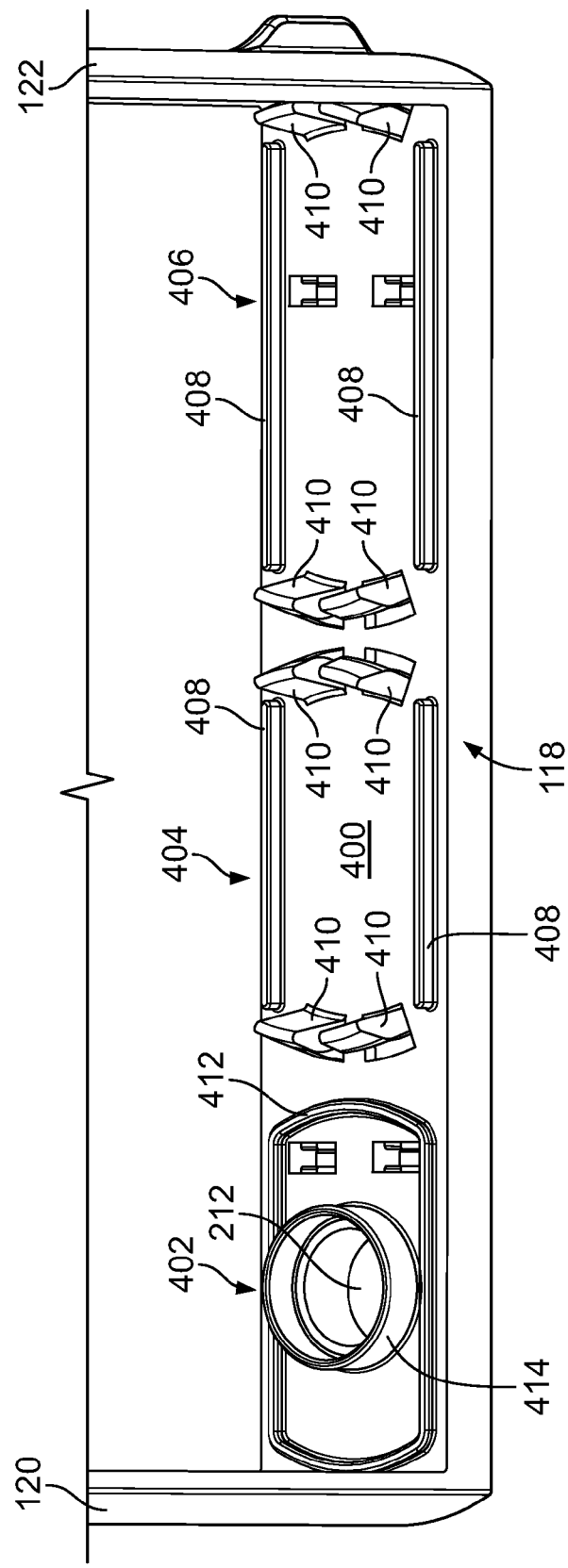
FIG. 4 illustrates a plurality of seats for the example containers of the example cartridge of FIGS. 1A-3.

FIG. 4 illustrates the example seat 118 of the carrier 110 of FIGS. 1A-3. In the illustrated example, the seat 118 includes a support surface 400, a first container support 402, a second container support 404 and a third container support 406. The second container 114 and the third container 116 couple to the seat 118 via the second container support 404 and the third container support 406, respectively. In the illustrated example, the second container support 404 and the third container support 406 include first protrusions 408 (e.g., ridges) and second protrusions 410 (e.g., posts). In the illustrated example, when the second container 114 and third container 116 are coupled to the seat 118, the second container 114 and the third container 116 rest on the support surface 400 and engage the first protrusions 408 and the second protrusions 410. The first protrusions 408 and the second protrusions 410 retain the second container 114 and the third container 116 and substantially prevent movement of the second container 114 and third container 116 relative to the carrier 110. In other examples, the carrier 110 employs additional and/or different protrusions, retaining members and/or devices to retain the second container 114 and/or the third container 116.

Figure 5:
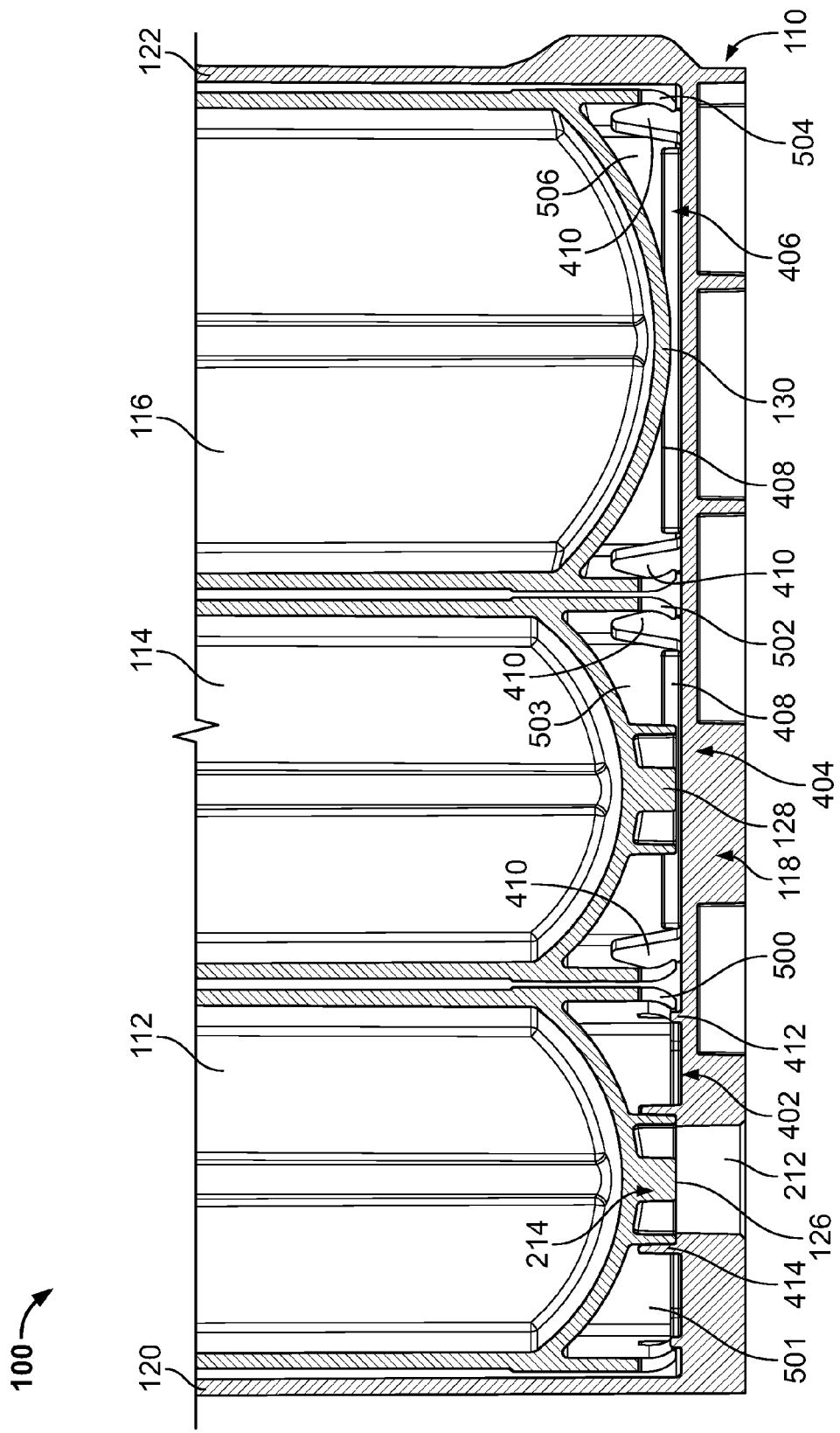
FIG. 5 is an enlarged view of the lower portion of the example containers and cartridge of FIG. 2 decoupled from the example carousel.

The example first container support 402 includes a third protrusion 412 (e.g., a ridge) to retain the first container 112 and/or substantially prevent the first container 112 from rotating relative to the carrier 110 when the first container 112 is in the locked position (e.g., an non-rotatable position) (FIG. 5). In the illustrated example, the third protrusion 412 is a ridge having a rounded-rectangular cross-sectional shape corresponding to the rounded-rectangular shape of the first container 112. In the illustrated example, the third protrusion 412 is raised to a first height relative to the support surface 400 of the seat 118. The example first container support 402 also includes an annular ridge or collar 414. In the illustrated example, the fourth aperture 212 is defined by the first container support 402 and the collar 414 is disposed on the support surface 400 about the fourth aperture 212. The example collar 414 provides a bearing surface, retains, supports, stabilizes, aligns and/or orients the first container 112 during operation of the example rotation mechanism 224 and the example carousel 102. The example collar 414 is raised to a second height relative to the support surface 400 greater than the first height. As described in greater detail below in conjunction with FIG. 7, when the cartridge 100 is placed onto the platform 104, the coupling 210 of the carousel 102 engages the first container 112 and lifts the first container 112 relative to the support surface 400 of the carrier 110 to an unlocked position in which the first container 112 is free to rotate via the coupling 210.

FIG. 5 is a cross-sectional view of the first end 126 of the example first container 112 when the first container 112 is in the lowered or locked position. In the illustrated example, the cartridge 100 is decoupled from the carousel 102 (e.g., during transport of the cartridge 100 to the platform 104). In the locked position, a first perimeter edge or rim 500 of the first container 112 is supported on the support surface 400 of the carrier 110. The first rim 500 of the first container 112 engages the third protrusion 412 such that the third protrusion 412 substantially prevents the first container 112 from rotating relative to the carrier 110 (e.g., the third protrusion 412 obstructs rotation of the first container 112). Thus, in the illustrated example, the first container 112 is non-rotatably coupled to the carrier 110 when the first container 112 is in the locked position. In some examples, a shape and size of the first rim 500 of the first container 112 substantially conforms to the shape of the third protrusion 412. In the illustrated example, the female connector 214 of the first container 112 is disposed in a space defined by the collar 414 (e.g., the fourth aperture 212), and the collar 414 is received in a groove 501 of the first container 112.

The example second container 114 includes a second rim 502 and a second groove 503. In the illustrated example, the second rim 502 engages the first protrusions 408 and the second protrusions 410 of the second container support 404 to couple the second container 114 non-rotatably to the carrier 110. The example third container 116 includes a third rim 504 and a third groove 506. In the illustrated example, the first protrusions 408 and the second protrusions 410 of the third container support 406 are disposed in the third groove 506 and engaged with the third rim 504 of the third container 116 to couple the third container 116 non-rotatably to the carrier 110.

Figure 6:
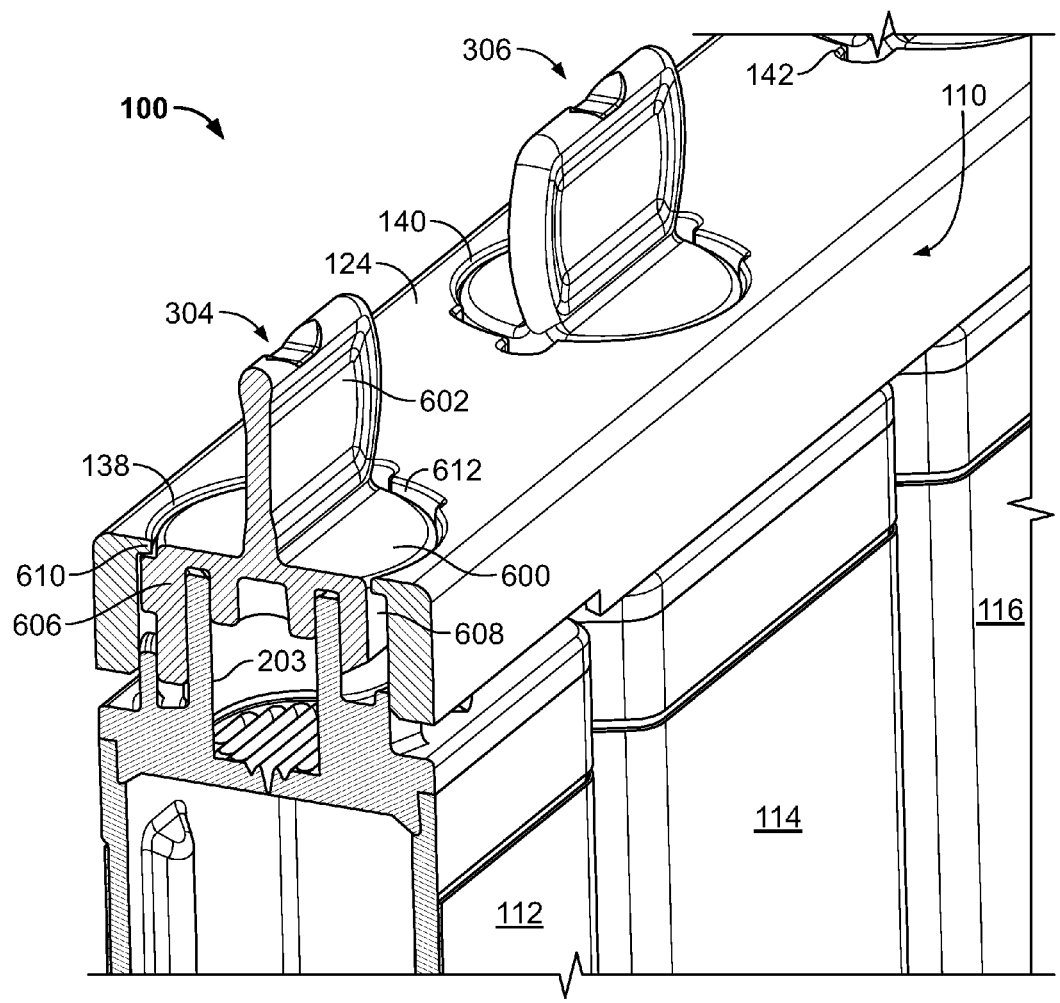
FIG. 6 is a perspective, cross-sectional view of a top portion of an example first container and the example cartridge taken along the B-B line of FIG. 3.

FIG. 6 is a cross-sectional view along the B-B line of FIG. 3 of the second end 132 of the first container 112 when the first container 112 is in the locked position. The example first cap 304 of FIG. 5 extends into the first aperture 138 of the cover 124 and is coupled to the throat 203 of the first container 112. The example first cap 304 includes a sealing portion 600 to cover 124 and/or seal the throat 203 of the first container 112. In the illustrated example, the first cap 304 includes a handle 602 coupled to the sealing portion 600. The handle 602 facilitates handling of the first cap 304, coupling and decoupling (e.g., removal) of the first cap 304 to the first container 112, etc.

When the first container 112 is coupled to the carrier 110 and the first cap 304 is coupled to the first container 112, the first cap 304 engages (e.g., contacts) the cover 124 to substantially hold or retain the first container 112 in the locked position. In the illustrated example, a fourth protrusion 606 extends from the sealing portion of the first cap 304. The example fourth protrusion 606 extends radially from a circumferential surface 608 of the sealing portion 600. The example cover 124 of the example carrier 110 includes a lip 610 extending into a portion of the first aperture 138. In the orientation of FIG. 6, the first cap 304 is in a first position such that the fourth protrusion 606 is disposed underneath the lip 610. Thus, when the first cap 304 is in the first position, the fourth protrusion 606 engages the lip 610 to substantially prevent the first container 112 from moving parallel to the second axis of rotation 144 relative to the carrier 110. For example, the fourth protrusion 606 may contact the lip 610 to prevent the first container 112 from being lifted above the third protrusion 412 (FIG. 5). Thus, in the illustrated example, the first cap 304 holds the first container 112 in engagement with the third protrusion 412, thereby retaining the first container 112 in the locked position.

Removal of the example first cap 304 enables the first container 112 to move from the lowered or locked position (FIG. 5) to a raised or unlocked position (FIG. 7) in which the first container 112 may rotate relative to the carrier 110. To remove the example first cap 304 of FIG. 6 from the first container 112, the first cap 304 is rotated until the fourth protrusion 606 is aligned in a notch or space 612 of the first aperture 138 clear of the lip 610 of the cover 124 (e.g., a slot in communication with the first aperture 138). The first cap 304 may then be removed from the first container 112 (e.g., via the handle 602). As described in greater detail below, when the first container 112 is in the unlocked position, the first container 112 can be lifted from the support surface 400 to enable rotation of the first container 112 relative to the carrier 110. The second cap 306 and the third cap 308 operate similarly to secure the second container 114 and the third container 116, respectively and to secure the position of cover 124.

Figure 7:
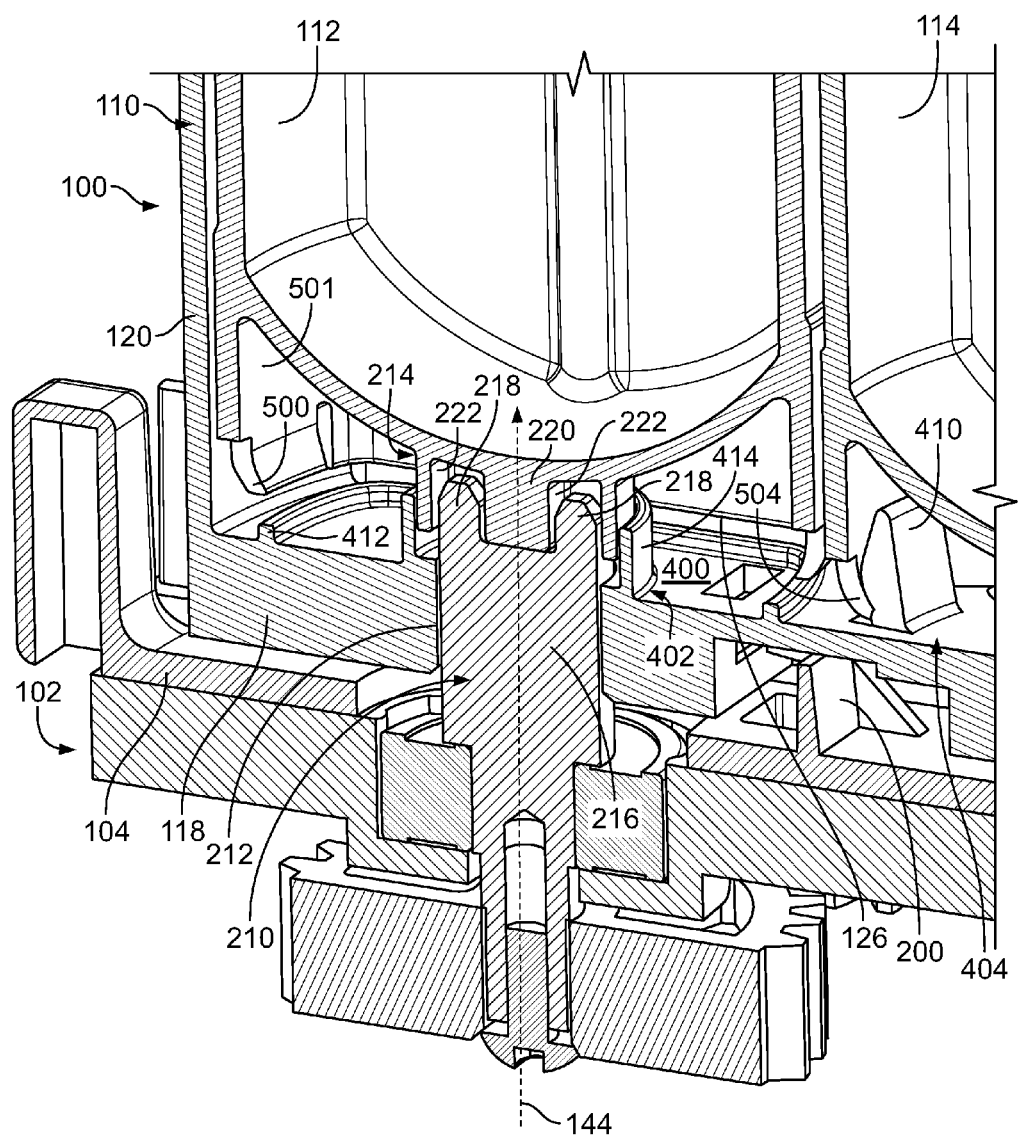
FIG. 7 is an enlarged view of the first container of FIG. 2 in an unlocked position.

FIG. 7 illustrates the example first container 112 in the unlocked position. In the illustrated example, the cartridge 100 is coupled to the carousel 102, and the first cap 304 is removed from the first container 112. The example coupling 210 of the carrier 110 extends through the fourth aperture 212 and moves (e.g., lifts or raises) the first container 112 along the second axis of rotation 144. In the illustrated example, the coupling 210 moves the first container 112 to a third height greater than the first height of the third protrusion 412 (FIGS. 4 and 5) and less than the second height of the collar 414. When the example first container 112 is lifted to the third height, the first rim 500 of the first container 112 disengages the third protrusion 412. As a result, the first container 112 is free to rotate about the second axis of rotation 144 (e.g., the third protrusion 412 does not obstruct rotation of the first container 112). In the illustrated example, the female connector 214 remains in the space defined by the collar 414 when the first container 112 is moved to the unlocked position. In some examples, as the first container 112 rotates relative to the carrier 110, the female connector 214 of the first container 112 and the collar 414 function as a bearing.

Figure 8:
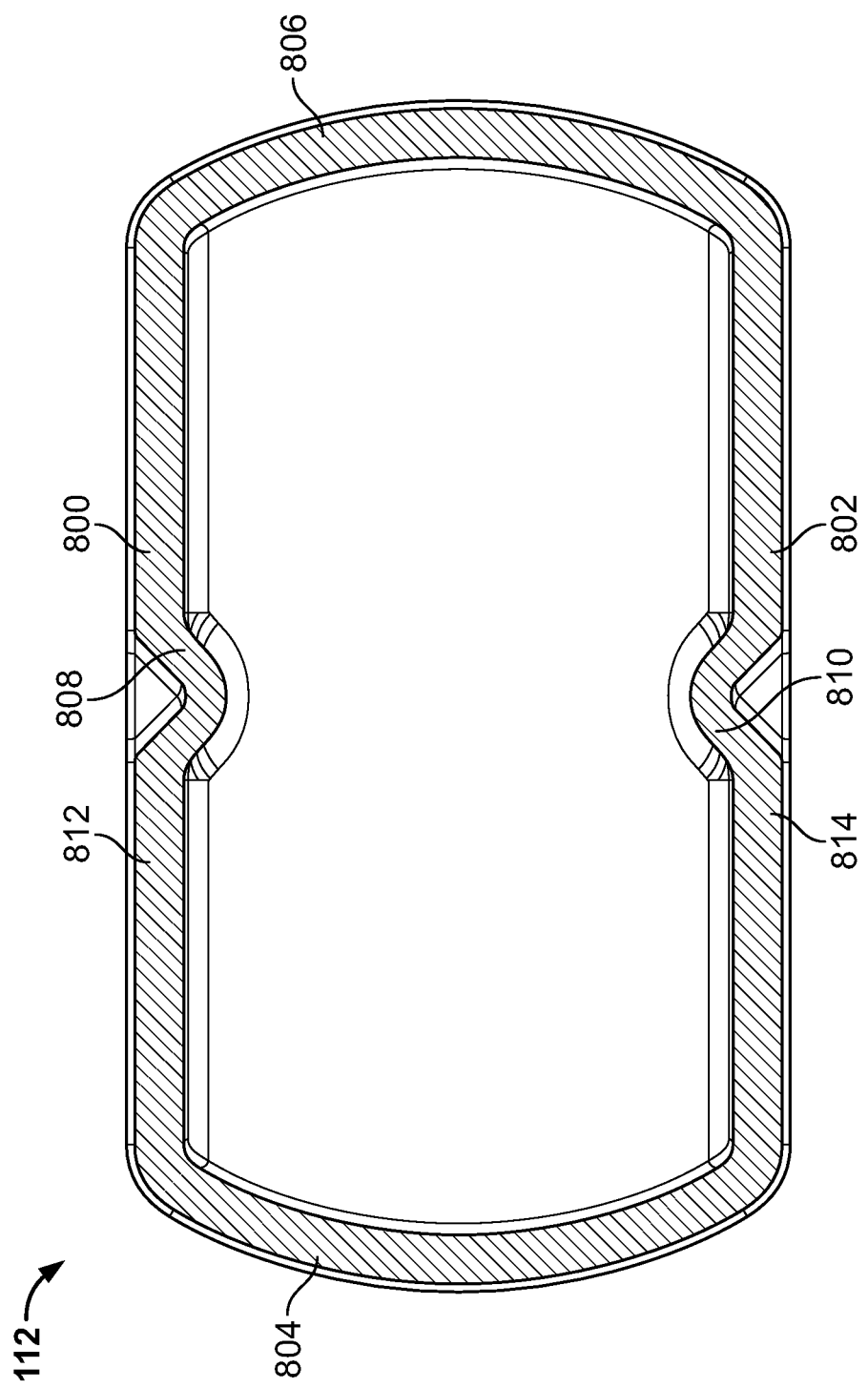
FIG. 8 is a top, cross-sectional view of the example first container taken along the C-C-line of FIG. 1A.

FIG. 8 is a cross-sectional view of the example first container 112 of FIGS. 1A-7 taken along the C-C line of FIG. 1A. In the illustrated example, the first container 112 includes a first sidewall 800, a second sidewall 802, a third sidewall 804 and a fourth sidewall 804. The first sidewall 800 is opposite the second sidewall 802. In the illustrated example, the first sidewall 800 includes a first rib 808 extending toward the second sidewall 802. The example second sidewall 802 includes a second rib 810 extending toward the first sidewall 800. The example first rib 808 and the example second rib 810 extend along the first sidewall 800 and the second sidewall 802, respectively, substantially parallel to the second axis of rotation 144. In the illustrated example, the first rib 808 and the second rib 810 are each disposed approximately equidistant from the third sidewall 804 and the fourth sidewall 806. The first rib 808 and the second rib 810 illustrated in FIG. 8 are merely examples. Thus, the first rib 808 and/or the second rib 810 may have other orientations, shapes, sizes, etc. in other examples. In some examples, the first sidewall 800 and/or the second sidewall 802 may include other numbers of ribs (e.g., 0, 2, 3, etc.). In addition, in some examples, one or more ribs may extend only partially down a wall, in an angled orientation relative to the second axis of rotation 144 and/or closer to one of the end walls 804, 806 than the other.

The example first container 112 has a rounded-rectangular shape. In the illustrated example, the first sidewall 800 is substantially parallel to the second sidewall 802. The example first sidewall 800 includes a first flat or planar portion 812, and the example second sidewall 802 includes a second flat or planar portion 814 parallel to the first planar portion 812. In the illustrated example, the third sidewall 804 is opposite the fourth sidewall 806 and the third sidewall 804 and the fourth sidewall 806 are curved. In the illustrated example, the third sidewall 804 and the fourth sidewall 806 curve outwardly relative to the longitudinal axis of the first container 112. In the illustrated example, a first distance between the first sidewall 800 and the second sidewall 802 is less than a second distance between the third sidewall 804 and the fourth sidewall 806. In other examples, the first distance is greater than or equal to the second distance. In some examples, the first container 112 has a depth (e.g., a distance from an outermost point of the first sidewall 800 to an outermost point on the second sidewall 802) of about 20 millimeters and a width (e.g., a distance from an outermost point on the third sidewall 804 to an outmost point on the fourth sidewall 806) of about 36 millimeters. Other examples have other dimensions. In other examples, the first container 112 has other shapes such as, for example, rectangular, square, cylindrical, triangular and/or other suitable shape(s) or combination of shape(s).

Figure 9:
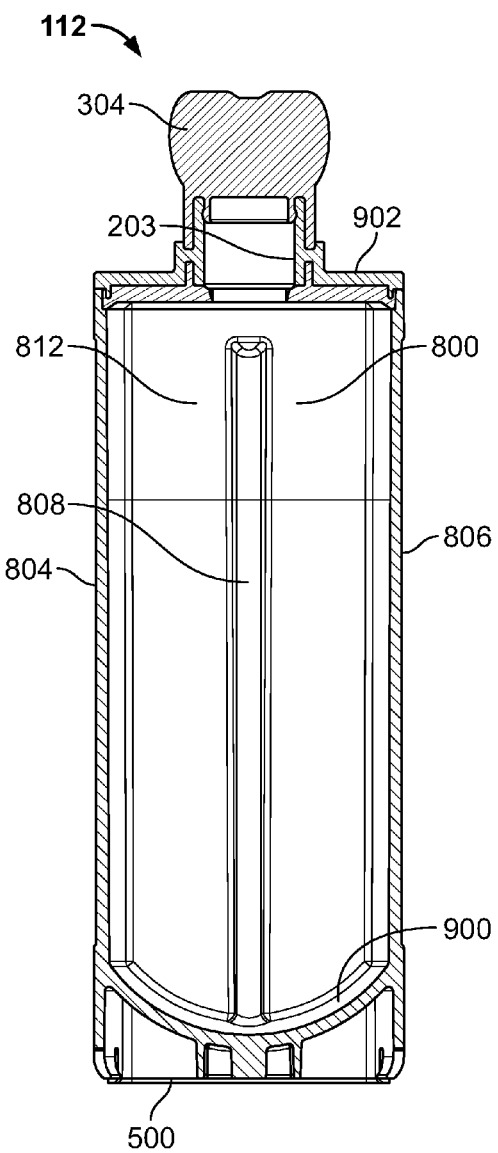
FIG. 9 is a cross-sectional view of the example first container taken along the D-D line of FIG. 3 and removed from the example cartridge.
Figure 10:
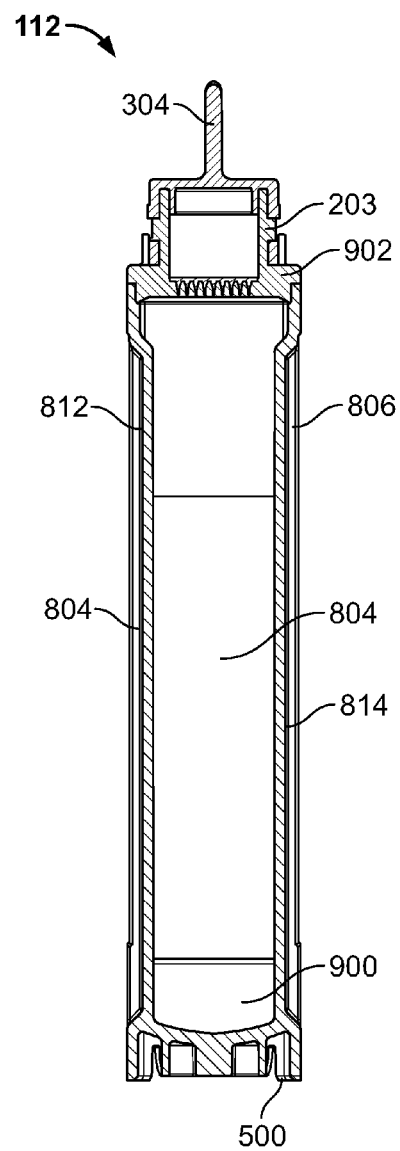
FIG. 10 is a side cross-sectional view of the example first container taken along the B-B line of FIG. 3 and removed from the example cartridge.

FIG. 9 is a cross-sectional view of the example first container 112 of FIGS. 1A-8 taken along the D-D line of FIG. 3 and removed from the cartridge 100. FIG. 10 is a cross-sectional view of the example first container 112 taken along the B-B line of FIG. 3, similar to FIG. 6, but showing the full length of the first container 112. Referring to FIG. 9, the example first container 112 includes a bottom wall 900 and a top wall 902 opposite the bottom wall 900. The example top wall 902 is coupled to the first sidewall 800, the second sidewall 802, the third sidewall 804 and the fourth sidewall 806. In the illustrated example, the top wall 902 is substantially planar. The throat 203 extends upwardly from the example top wall 902 in the orientation of FIG. 9. In the illustrated example, a height of the first container 112 excluding the throat 203 and the first cap 304 (e.g., from an outermost point of the first rim 500 to an outmost point on the top wall 902) is about 94 millimeters. Other examples may include heights.

The example bottom wall 900 of FIG. 9 is coupled to the first sidewall 800, the second sidewall 802, the third sidewall 804 and the fourth sidewall 806. In the illustrated example, the bottom wall 900 is bowed or curved away from the top wall 902 about a first axis passing through the first sidewall 800 and the second sidewall 802. Thus, the bottom wall 900 is convex when viewed from outside of the container 112 (e.g., from the bottom exterior of the container 112) or concave when viewed from inside of the container 112. The example bottom wall 900 is also bowed or curved away from the top wall 902 about a second axis passing through the third sidewall 804 and the fourth sidewall 806. Thus, the example bottom wall 900 forms a bowl-like structure.

In some examples, the first container 112 is at least partially filled with a reagent including solid particles (e.g., latex coated paramagnetic particles). Some of the particles in the liquid may settle and rest on the bottom wall 900 (e.g., during transport of the cartridge 100 to the carousel 102). During operation of the carousel 102, the first container 112 moves about the first axis of rotation 106 (e.g., in the back-and-forth motion) and the second axis of rotation 144 to agitate the liquid and/or disperse the particles in the liquid. For example, when the first container 112 is moved via the carousel 102, curvatures of the bottom wall 900 direct the liquid and/or the particles on or near the bottom wall 900 to move (e.g., flow) toward the top wall 902, thereby agitating the liquid and dispersing the particles. Further, movement of the sidewalls 800, 802, 804, 806, the first rib 808 and/or the second rib 810 with and/or relative to the liquid agitates the liquid and disperses the particles. In some examples, the first container 112 agitates the liquid such that the particles are substantially uniformly dispersed within the liquid during operation of the carousel 102.

Figure 11:
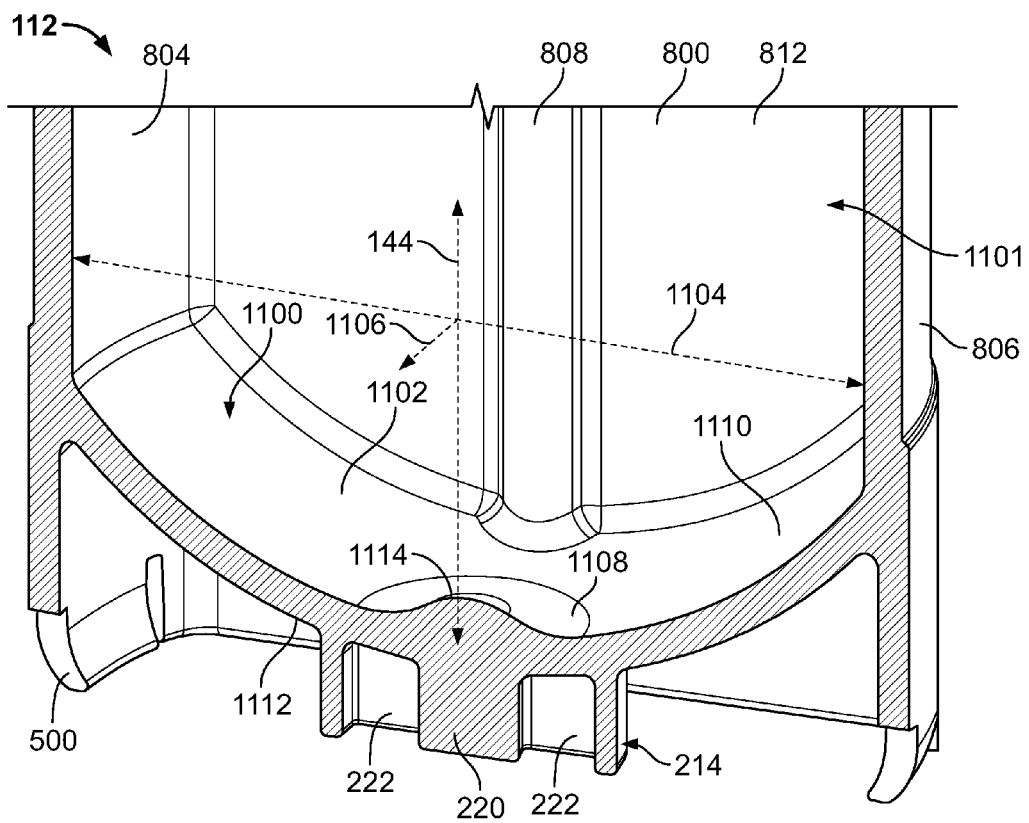
FIG. 11 illustrates an alternative bottom wall of the example first container of FIGS. 6-9.
Figure 12:
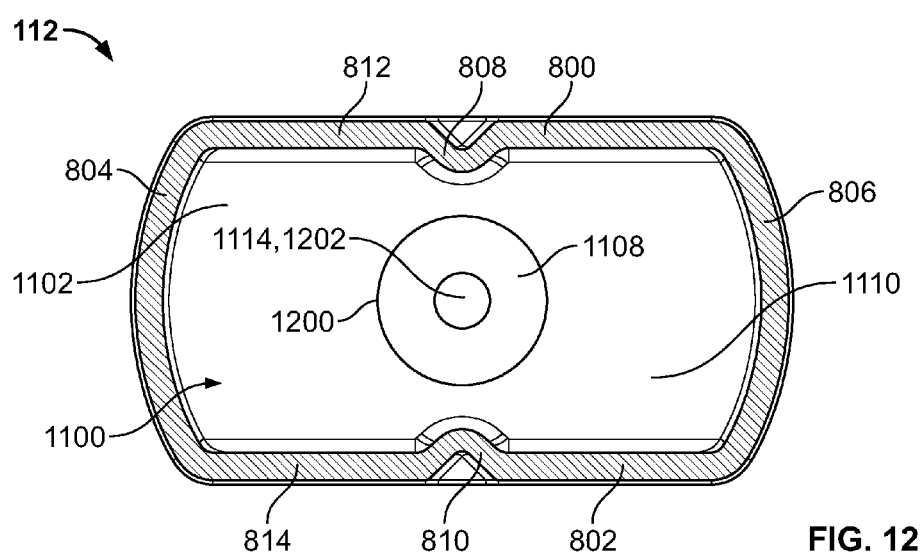
FIG. 12 is a top view of the example bottom wall of FIG. 11.

FIGS. 11-12 illustrate the first container 112 having an alternative bottom wall 1100 disclosed herein. FIG. 11 is a perspective, cross-sectional view of a lower portion of the first container 112 showing the example bottom wall 1100. In the illustrated example, the sidewalls 800, 802, 804, 806, the top wall 902 and the bottom wall 1100 define a cavity 1101 to receive and hold liquid. In the illustrated example, the bottom wall 1100 includes a basin or concave portion 1102 (when viewed from inside the container 112) extending from first sidewall 800 to the second sidewall 802 and from the third sidewall 804 to the fourth sidewall 806. The example concave portion 1102 bows outward away from the top wall 902 about a first axis 1104 and a second axis 1106 (e.g., axes perpendicular to each other and to the second axis of rotation 144). In some examples, the concave portion 1102 is a bowl-like or semispherical structure.

The example bottom wall 1100 also includes a bulge or protrusion 1108 extending from a first side 1110 of the bottom wall 1100 toward the top wall 902 (e.g., extending into the cavity 1101). In the illustrated example, the post 220 of the female connector 214 is aligned with the protrusion 1108 and depends from a second side 1112 of the bottom wall 1100 opposite the first side 1110. In the illustrated example, the protrusion 1108 is a convexity (e.g., a rounded or curved protrusion or bulge) having a crest or apex 1114. Thus, the example bottom wall 1100 of FIG. 11 includes the concave portion 1102 and a convex portion (e.g., the example protrusion 1108). In other examples, the protrusion 1108 has other shapes (e.g., cone-shaped, pyramid-shaped, etc.). The example protrusion 1108 of FIG. 12 has a first radius of curvature and the example concave portion 1102 has a second radius of curvature. In the illustrated example, the first radius of curvature is less than the second radius of curvature. Also, in the illustrated example, the first radius of curvature and the second radius of curvature of disposed in opposite directions.

FIG. 12 is a top view of the example bottom wall 1100 of FIG. 11. In the illustrated example, the protrusion 1108 has a substantially circular base 1200 disposed on a center 1202 of the bottom wall 1100. In the illustrated example, the center 1202 of the bottom wall 1100 is along the second axis of rotation 144. Thus, when the example first container 112 rotates about the second axis of rotation 144, the bottom wall 1100 rotates about the second axis of rotation 144. The apex 1114 of the example protrusion 1108 is also disposed on the center 1202 of the bottom wall 1100 and, thus, the apex 1114 is disposed along the second axis of rotation 144 in the illustrated example. As a result, the protrusion 1108 slopes downward from the second axis of rotation 144.

When the example first container 112 rotates about the second axis of rotation 144, particles disposed in a liquid in the first container 112 along the second axis of rotation 144 may experience little or no centrifugal force. As a result, these particles may settle onto or near the protrusion 1108 of the bottom wall 1100. In the illustrated example, when the particles settle onto the protrusion 1108 of the bottom wall 1100, the particles slide and/or roll on the protrusion 1108 away from the apex 1114. As a result, the particles move toward the sidewalls 800, 802, 804, 806 where centrifugal force facilitates uniform dispersion of the particles in the liquid.

Figure 13:
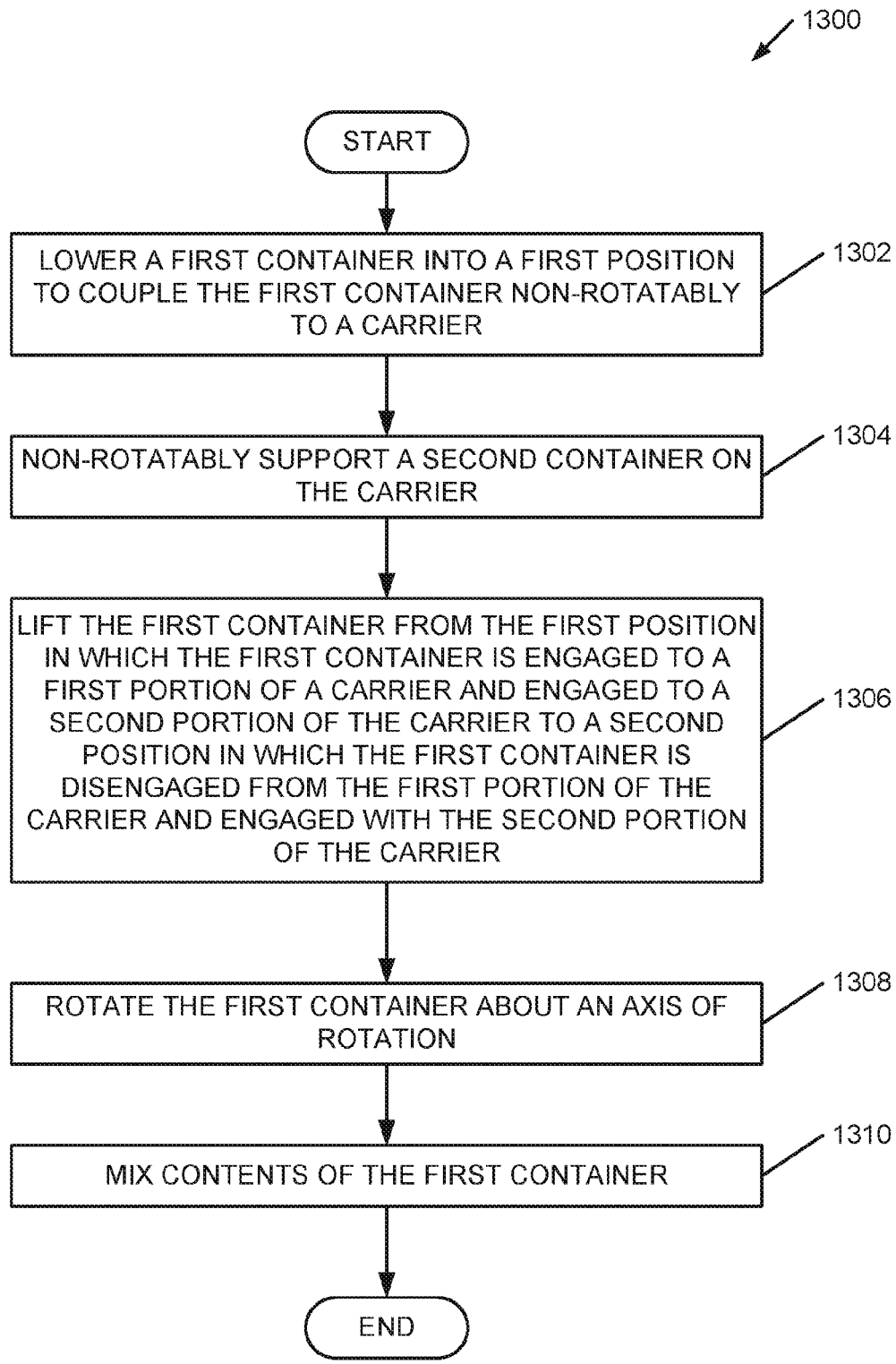
FIG. 13 is a flowchart representative of an example method disclosed herein.

A flowchart representative of an example method is shown in FIG. 13. Although the example process is described with reference to the flowchart illustrated in FIG. 13, many other methods may alternatively be used. For example, the order of execution of the blocks may be changed, and/or some of the blocks described may be changed, eliminated, or combined.

The method of FIG. 13 begins at block 1302 by lowering the first container 112 into a first position to couple the first container 112 non-rotatably to the carrier 110. For example, the first container 112 of FIGS. 1A-12 may be lowered onto the first container support 402 of the seat 118 of the carrier 110. In some such examples, first container 112 engages a first portion of the carrier 110 and a second portion of the carrier 110 in the first position. For example, the first rim 500 engages the third protrusion 412, and the female connector 214 engages the collar 414. In some examples, the first cap 304 is coupled to the first container 112 to hold or retain the first container 112 in the first position.

At block 1304, the second container 114 is non-rotatably supported on the carrier 110. In some examples, the second container 114 is coupled non-rotatably to the second container support 404 via the first protrusions 408 and the second protrusions 410 of the second container support 404. In some examples, the third container 116 is also non-rotatably supported on the carrier 110 via the first protrusions 408 and the second protrusions 410 of the third container support 406.

At block 1306, the first container 112 is lifted from the first position to a second position in which the first container 112 is disengaged from the first portion of the carrier 110 while engagement with the second portion of the carrier 110 is maintained. For example, the first container 112 may be lifted to the third height from the supporting surface by the example coupling 210 of the carousel 102. When the cartridge 100 is coupled to the carousel 102, the coupling 210 extends into the fourth aperture 212 and lifts the first container 112 to the third height. When the first container 112 is lifted to the third height, the first rim 500 disengages the third protrusion 412 and the female connector 214 is disposed in the space defined by the collar 414.

At block 1308, the first container 112 is rotated (e.g., oscillated and/or spun) about an axis of rotation. In some examples, the first container 112 is rotated about the first axis of rotation 106 with the platform 104 and about the second axis of rotation 144 via the coupling 210. At block 1310, contents of the first container 112 are mixed. For example, liquid and/or particles in the container are agitated by the planar portions of the first side-wall 800 and/or the second sidewall 802. In some examples, the contents of the first container 112 are also mixed by a bottom protrusion of the container such as, for example, the protrusion 1108 of the bottom wall 1100 of FIGS. 11 and 12. In some examples, the contents of the first container 112 are mixed such that the particles are substantially uniformly dispersed in the liquid in the first container 112.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus comprising:
    a carrier having a base, the base including:
        a ridge extending from the base; and
        a collar extending from the base; and
    a container supported on the base, the container movable between (A) a locked positon in which the ridge fixedly engages the container to non-rotatably couple the container to the base and (B) an unlocked position in which the container is disengaged from the ridge and the container is rotatable about the collar.

2. The apparatus of claim 1, wherein the ridge extends from the base a first distance and the collar extends from the base a second distance greater than the first distance.

3. The apparatus of claim 2, wherein, in the unlocked position, the container is raised a third distance away from the base, the third distance being between the first distance and the second distance.

4. The apparatus of claim 1, wherein the container includes a rim extending from a bottom of the container, and wherein the ridge is to engage the rim when the container is in the locked position.

5. The apparatus of claim 1, wherein the container includes a connector extending from a bottom of the container, the connector disposed within the collar in the locked position and the unlocked position.

6. The apparatus of claim 5, wherein the connector is a first connector, and wherein the base of the carrier includes an opening extending through the collar and aligned with the first connector of the container, the opening to receive a second connector to engage the first connector and move the container between the locked positon and the unlocked position.

7. The apparatus of claim 1, wherein the container includes a throat extending from a top of the container, the throat having a first opening to receive a pipette to aspirate or dispense a liquid from the container.

8. The apparatus of claim 7, wherein the carrier includes a cover disposed over the top of the container.

9. The apparatus of claim 8, wherein the cover includes a second opening aligned with the first opening.

10. The apparatus of claim 9, wherein the throat is at least partially disposed in the second opening.

11. The apparatus of claim 10, wherein the throat is slidable in the second opening when the container is moved between the locked position and the unlocked position.

12. The apparatus of claim 10, wherein the throat is rotatable in the second opening when the container in the unlocked position.

13. The apparatus of claim 10, further including a cap to be coupled to the throat of the container, the cap extending at least partially into the second opening of the cover when the cap is coupled to the throat.

14. The apparatus of claim 1, wherein the container is a first container, further including a second container non-rotatably coupled to the base.

15. The apparatus of claim 14, wherein the ridge and the collar define a first container support to retain the first container, the base further including a second container support to retain the second container.

16. The apparatus of claim 15, wherein the ridge is a first ridge, and wherein the second container support includes a second ridge to engage the second container to non-rotatably couple the second container to the base.

17. The apparatus of claim 15, further including a third container, the base further including a third container support to retain the third container.

18. The apparatus of claim 1, wherein the container has a rounded rectangular shape.

* * * * *

UNITED STATES PATENT AND TRADEMARK OFFICE
CERTIFICATE OF CORRECTION

PATENT NO. : 9,789,454 B2
APPLICATION NO. : 15/347556
DATED : October 17, 2017
INVENTOR(S) : Robert Paul Luoma, II Page 1 of 1

It is certified that error appears in the above-identified patent and that said Letters Patent is hereby corrected as shown below:

On the Title Page

In the abstract, Line 6: Replace "positon" with --position--.

In the Claims

Column 13, Line 19 (Claim 1): Replace "positon" with --position--.

Column 14, Line 3 (Claim 6): Replace "positon" with --position--.

Signed and Sealed this
Twentieth Day of February, 2018

Andrei Iancu
*Director of the United States Patent and Trademark Office*